(12) United States Patent
Lesniak

(10) Patent No.: US 7,658,193 B2
(45) Date of Patent: Feb. 9, 2010

(54) INTEROCCLUSAL APPLIANCE AND METHOD

(75) Inventor: Frank Lesniak, Media, PA (US)

(73) Assignee: Hayloft Enterprises, Inc., Wilmington, DE (US)

( * ) Notice: Subject to any disclaimer, the term of this patent is extended or adjusted under 35 U.S.C. 154(b) by 57 days.

(21) Appl. No.: 11/757,490

(22) Filed: Jun. 4, 2007

(65) Prior Publication Data

US 2008/0295850 A1    Dec. 4, 2008

(51) Int. Cl.
*A61C 7/08* (2006.01)
*A61C 5/14* (2006.01)

(52) U.S. Cl. .................. 128/862; 128/859; 128/861; 433/6

(58) Field of Classification Search ............ 128/848, 128/859, 861, 862; 433/6
See application file for complete search history.

(56) References Cited

U.S. PATENT DOCUMENTS

| | | |
|---|---|---|
| 2,750,941 A | 6/1956 | Cathcart |
| 3,234,942 A | 2/1966 | Simor |
| 3,312,218 A | 4/1967 | Jacobs |
| 3,333,582 A | 8/1967 | Cathcart |
| D215,685 S | 10/1969 | Helmer |
| 3,924,638 A | 12/1975 | Mann |
| D302,724 S | 8/1989 | Huffman |
| 5,562,106 A | 10/1996 | Heeke et al. |
| 5,566,684 A | 10/1996 | Wagner |
| 5,826,581 A | 10/1998 | Yoshida |
| 5,836,761 A | 11/1998 | Belvedere et al. |
| D406,405 S | 3/1999 | Yoshida |
| 5,879,155 A | 3/1999 | Kittelsen |
| 6,012,919 A | 1/2000 | Cross, III et al. |
| 6,302,110 B1 | 10/2001 | Yoshida et al. |
| 6,371,758 B1 | 4/2002 | Kittelsen |
| 6,397,848 B1 * | 6/2002 | Kagekata et al. ............ 128/862 |
| 6,491,036 B2 | 12/2002 | Cook |
| 6,691,710 B2 | 2/2004 | Kittelsen et al. |
| D492,785 S | 7/2004 | Garabito |
| 6,820,623 B2 | 11/2004 | Cook |
| 6,830,051 B1 | 12/2004 | Lesniak et al. |
| D504,744 S | 5/2005 | Hidalgo et al. |
| 7,047,978 B2 * | 5/2006 | Zuk ........................... 128/848 |
| D541,481 S | 4/2007 | Farrell |

(Continued)

FOREIGN PATENT DOCUMENTS

DE    1607433 U    6/1950

(Continued)

*Primary Examiner*—Patricia Bianco
*Assistant Examiner*—Keri J Nicholson
(74) *Attorney, Agent, or Firm*—Connolly Bove Lodge & Hutz LLP

(57) ABSTRACT

An interocclusal appliance is formed from a single polymer material composition as one unitary piece or from multiple polymer material compositions as a two-piece preform. The two-piece preform includes a base material and an impression material that has a softening point lower than the base material. Teeth are received into the heat-softened impression material, so as to contour the impression material. A portion of the impression material also may contour to a portion of the user's palate. In certain embodiments, substantially no polymeric material contacts the front surfaces of the front teeth, leading to greater comfort and better air flow between front teeth. In still another embodiment, the appliance fits over front teeth only and no polymeric material contacts the maxillary molars.

47 Claims, 8 Drawing Sheets

U.S. PATENT DOCUMENTS

| | | |
|---|---|---|
| 7,210,483 B1 | 5/2007 | Lesniak et al. |
| 2006/0011204 A1 | 1/2006 | Maher |
| 2006/0078840 A1 | 4/2006 | Robson |
| 2008/0138755 A1 | 6/2008 | Jansheski et al. |
| 2008/0138766 A1 | 6/2008 | Jansheski |

FOREIGN PATENT DOCUMENTS

| | | |
|---|---|---|
| EP | 0359135 | 3/1990 |

* cited by examiner

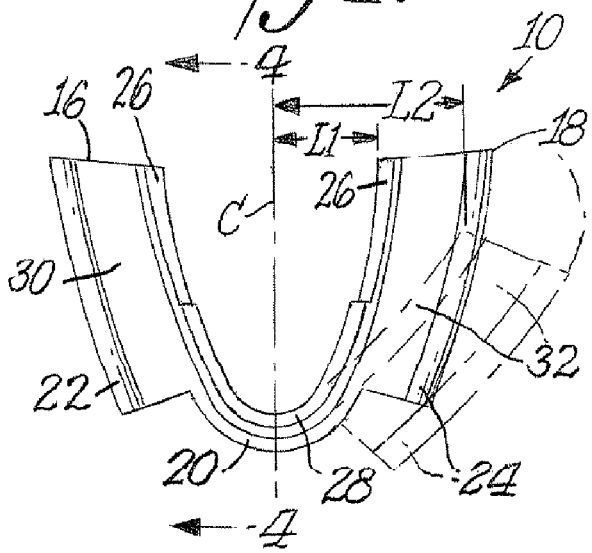
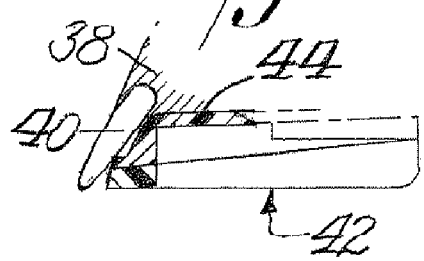
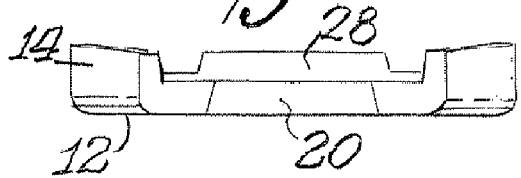
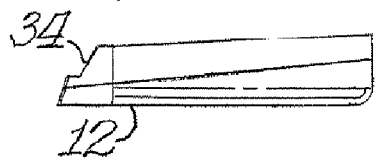
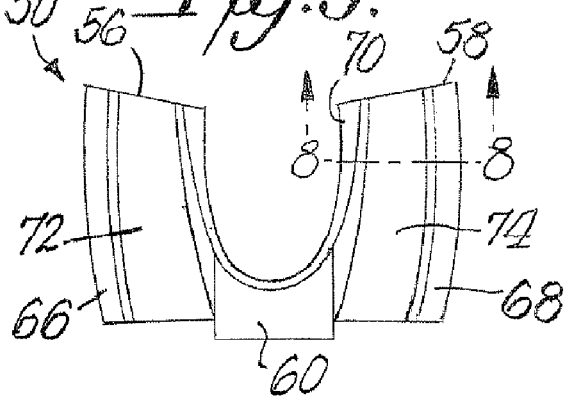
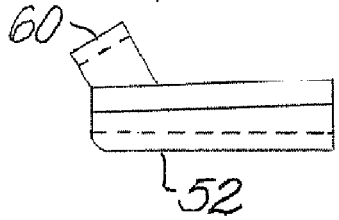
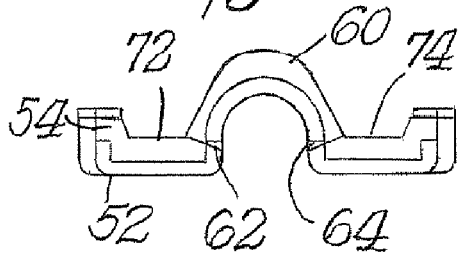
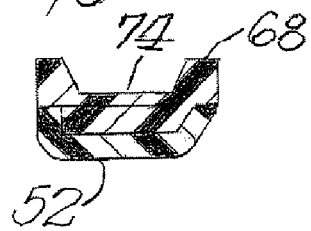

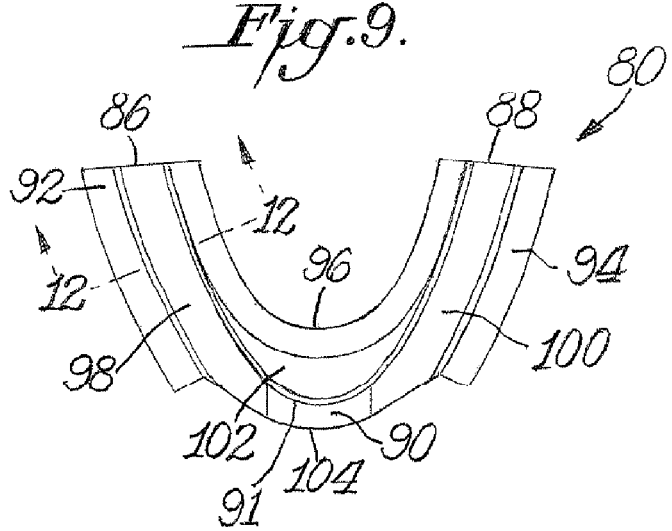
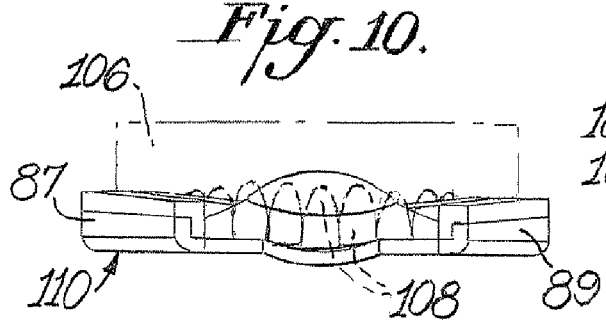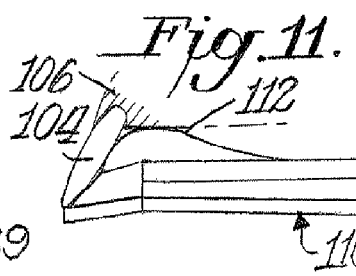
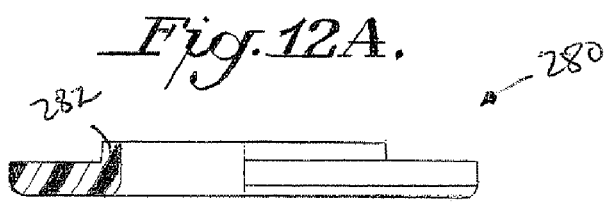

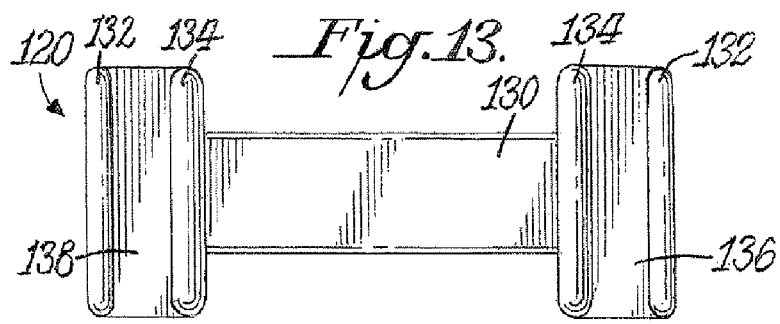
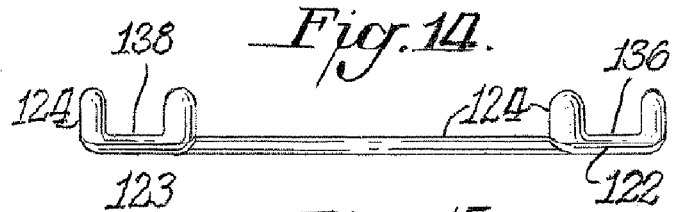
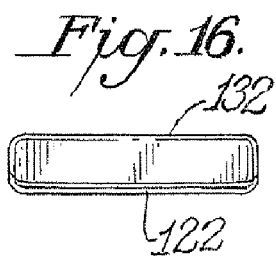
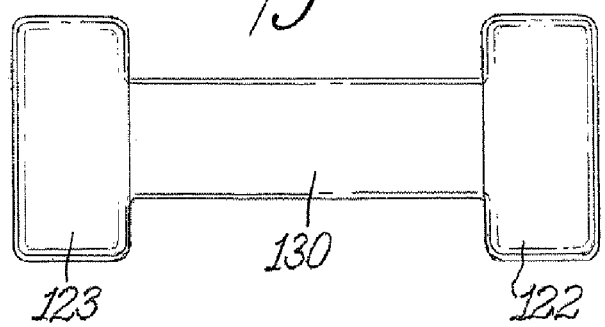
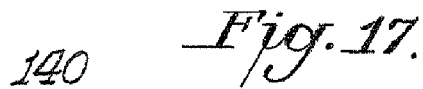
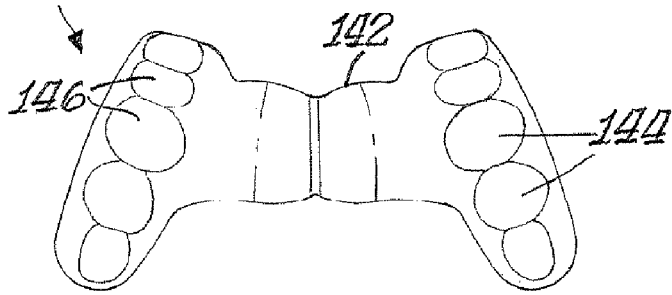
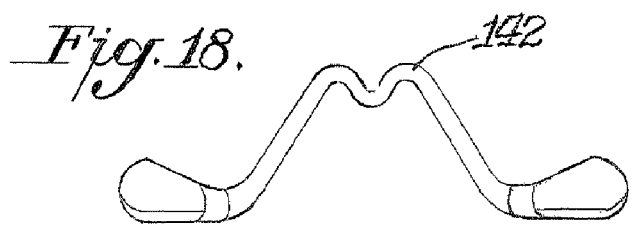
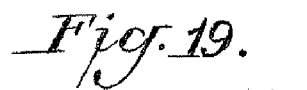

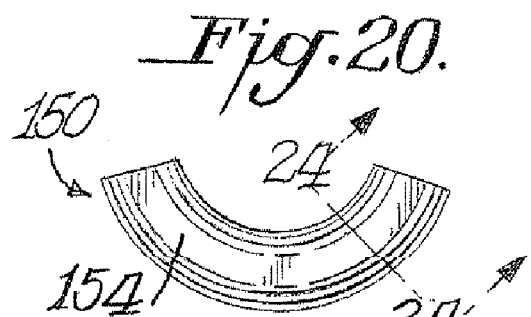
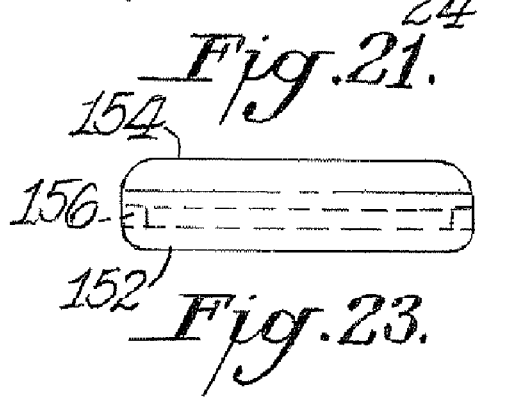
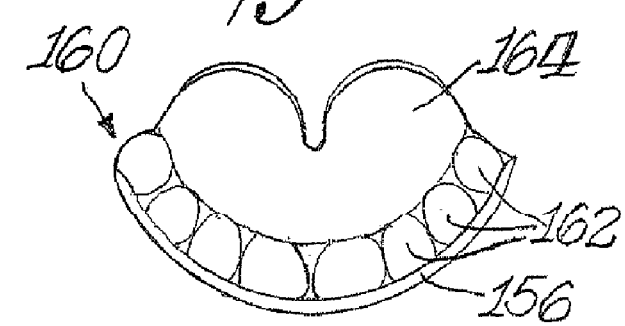
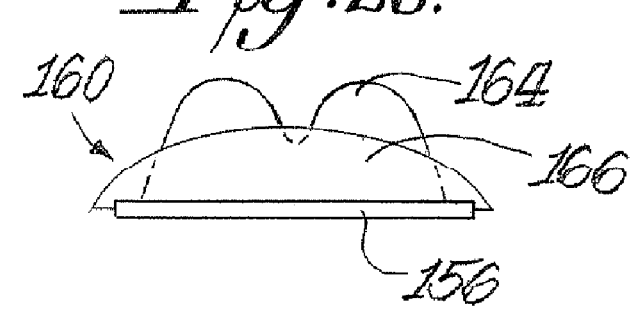

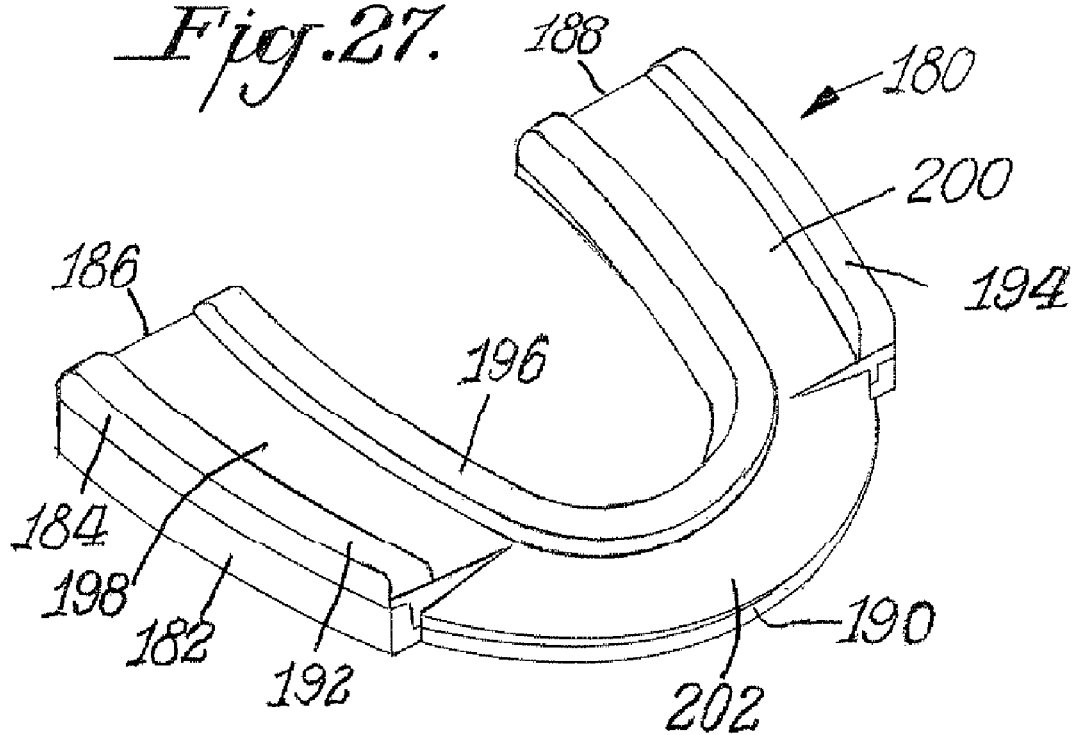
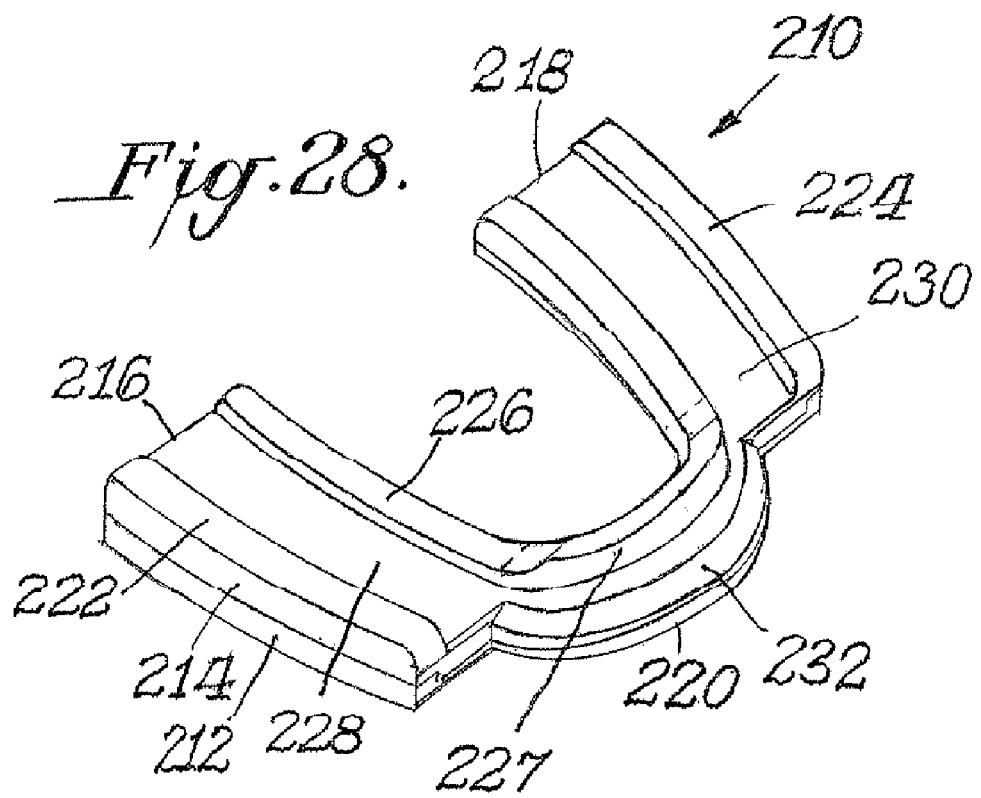

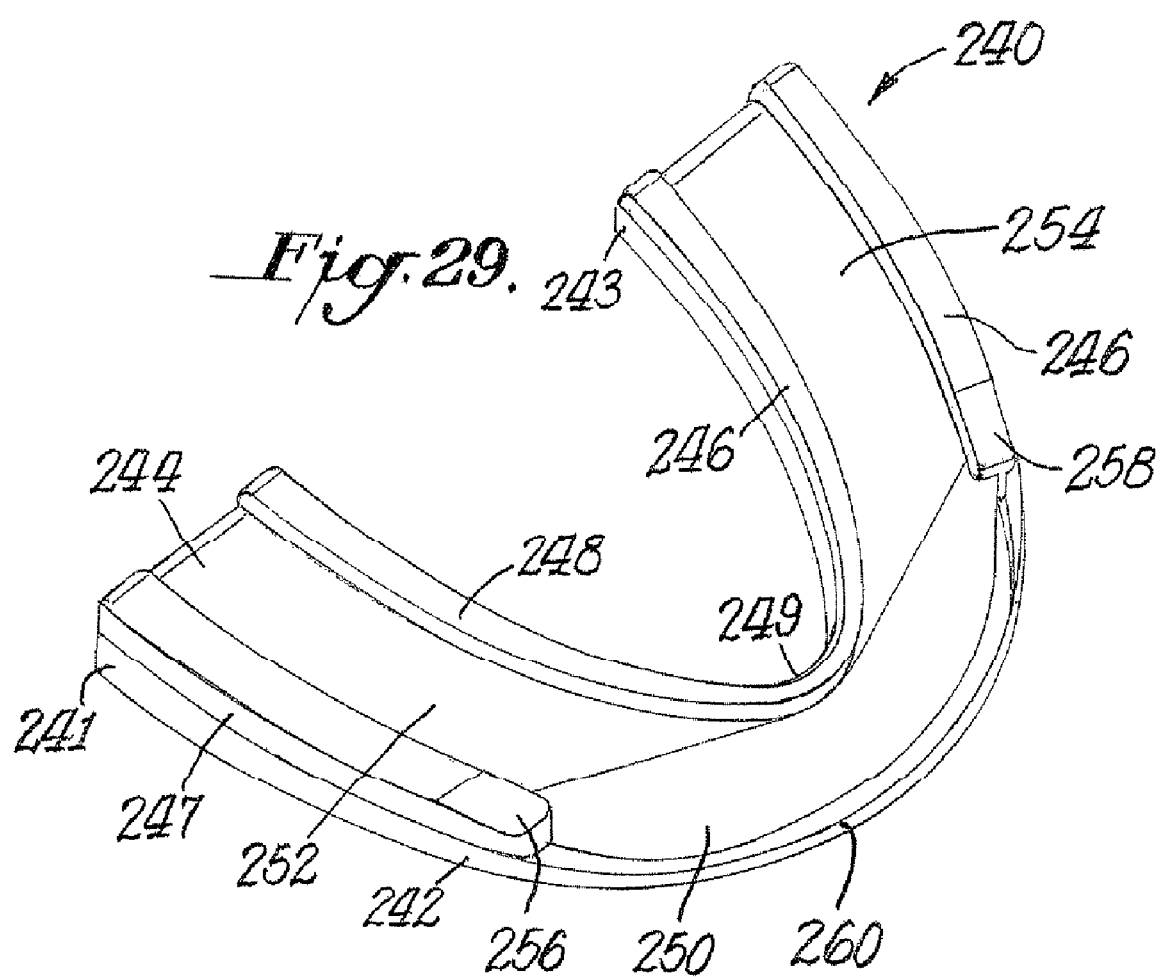

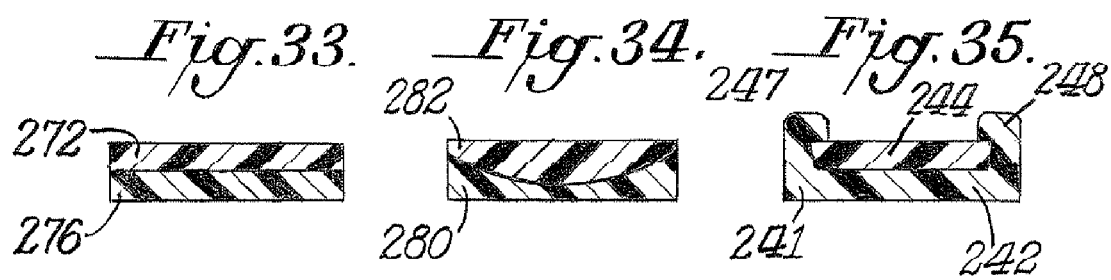
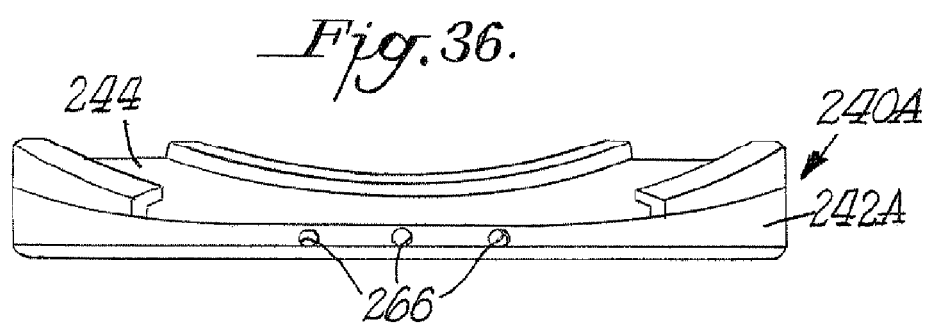

INTEROCCLUSAL APPLIANCE AND METHOD

BACKGROUND OF THE INVENTION

1. Field of the Invention

This invention relates to interocclusal appliances worn in the mouth to prevent tooth structure loss resulting from subconscious parafunctional mandibular habits known as bruxism or clenching.

2. Description of the Prior Art

Bruxism has been found to be a major factor in occlusal tooth surface wear, and may be a significant potential risk factor for dental implant failure. Interocclusal appliances, such as mouth guards or nightguards, have been recognized as beneficial to alleviate the adverse effects of bruxism and clenching.

Prior interocclusal appliances include those that are fitted by a dental professional and those that are self-fitted. Professionally fitted interocclusal appliances are molded of relatively hard acrylic resin from casts of the patient's mouth taken from a dental impression. This procedure requires multiple visits to the dental professional's office, and thus is time-consuming and expensive.

Self-fitted interocclusal appliances typically include a thermoplastic channel or trough in the shape of a maxillary arch. A thermoplastic impressionable liner material is carried in the trough. Such thermoplastic impressionable liner material has a softening point lower than that of the trough. The liner is softened by immersing it in hot water. Then, the liner is molded to conform to a user's mount/teeth by inserting the heated liner into the user's mouth, placing it against the maxillary arch. The user's jaw is closed and biting pressure is applied to force the maxillary teeth into the liner. Representative self-fitted interocclusal appliances of this type are shown in U.S. Pat. Nos. 5,566,684; 6,302,110; and 6,820,623; and European Patent Application No. EP 0 359 135 A1.

Problems were encountered with these prior self-fitting nightguards. Home users had some difficulty fitting the appliance to their own teeth. It can be difficult to properly center and align (register) the heated impressionable liner material of the nightguard relative to one's own maxillary arch. If the fit is not proper, the user could experience discomfort on wearing the nightguard and/or the nightguard could prematurely wear out. In addition, in some prior nightguards, the thermoplastic impressionable liner material was used without a backing plate. Upon severe bruxing or clenching, many users would bite through this material, thus wearing out the appliance and losing the benefit of protecting teeth surfaces. In other prior nightguards, the thermoplastic impressionable liner material separated from the trough as a result of shearing forces from a user's severe bruxing or clenching.

U.S. Pat. No. 6,830,051 illustrates an improved self-fitting interocclusal appliance that includes an impression material unitarily molded to a base material, creating a high shear resistance bond between components. In this prior appliance, the lower base has the shape of a maxillary dental arch. An impression preform of a softenable thermoplastic is molded to the lower base. The inner side walls of the appliance may be tapered inwardly to facilitate proper placement of the appliance in the user's mouth over the user's upper teeth. This appliance thus fits over all upper teeth of the maxillary arch.

Many of the prior self fitting interocclusal appliances include thermoplastic material over all upper teeth of the maxillary arch, including molars and front teeth (incisors and eye teeth). Plastic material between the front lip and front teeth can be uncomfortable. Moreover, when such an appliance is worn, no space or yap is left between the top and bottom teeth. For example, a person's natural bite would generally leave a gap between the upper incisors and the lower incisors. The lack of this gap can lead to breathing difficulties for users accustomed to more mouth breathing at night, such as users who have frequent nasal congestion. An appliance that does not cover or does not substantially cover front teeth, particularly the incisors, would be more comfortable. In addition, when circumstances permit, an appliance that permits greater air flow between upper and lower front teeth would be more comfortable.

For some users, the excess material in an appliance extending over the back molars and/or between the back molars and the cheeks is not comfortable. Such users seek an appliance that satisfactorily protects teeth surfaces without covering all teeth of the maxillary arch. Thus, another alternative appliance with such characteristic would be more comfortable for these users.

SUMMARY OF INVENTION

In a first embodiment of the invention, a one-piece interocclusal appliance for fitting over maxillary teeth of a user is fabricated from a polymeric material formed in a configuration generally of a dental arch having a bottom plan surface and having two end portions and a central portion together forming said dental arch. The end portions each define receiving portions for receiving at least one maxillary molar, and the central portion is shaped so as to be disposed behind at least some of the user's front teeth. In this embodiment the interocclusal appliance lacks substantial material in front of the user's front teeth. To facilitate fitting, the end portions of the dental arch may be spaced further from one another by flexing the polymeric material. The appliance may be heat and fit, such as by heating the polymeric material to a temperature that is above its Vicat softening temperature so that the receiving portions may be molded into cavities for receiving the maxillary molars, and the central portion may be shaped to conform to a portion of the user's palate behind one or more of the user's front teeth. Once fitted, the appliance is maintained in fitted position in the user's mouth over the user's maxillary molars until the user elects to remove said appliance from the mouth.

Certain features may be included to help locate the appliance in the user's mouth during fitting. For example, the central portion may include a preformed upstanding bridge or arch between the end portions. In addition, a slanted ledge may be formed at the central portion. As another example, a front tooth guide may extend generally upwardly from a top surface of the dental arch at the central portion. The front tooth guide may comprise a continuous or discontinuous arcuate ridge, or a series of one or more projections. As yet another example, a pilot channel may be formed in the end portions between inner and outer upstanding ridges that extend generally upwardly from a top surface of the dental arch.

The interocclusal appliance may be formed from a polymeric material, such as polymeric materials having Shore A hardness of at least about 20, or combinations of such materials. Materials meeting this criteria include ethylene methyl acrylate (EMA) copolymers, ethylene vinyl acetate (EVA) copolymers, acrylics, high density polyethylenes (HDPE), styrenics (IMPS), acrylonitrile-butadiene-styrene (ABS) copolymers, poly(methylmethacrylates) (IM-PMMA), alpha-polyolefins and mixtures thereof. Other FDA-approved polymeric materials may be suitable. The hardness, strength or color of the material forming the appliance may be altered by incorporating one or more types of particles, including nanoparticles, into the polymeric material. Such particles may be included to help a user monitor the wear or degradation of the material forming the appliance.

Another embodiment of an interocclusal appliance for fitting over maxillary or mandibular teeth of a user according to the invention has two components, a base and an impression material. The two components together initially comprise a preform that may be fitted and formed into the interocclusal appliance. The base generally has a top surface and a bottom surface, where the bottom plan surface is in a configuration of a dental arch having two end portions and a central portion together forming said dental arch. Impression material is bonded (such as by molding or adhering) to the top surface of the base, with said impression material defining receiving portions in the end portions of the base for receiving one or more molars at each end portion. The impression material comprises a polymeric material that has a Vicat softening temperature, and said base comprises a polymeric material that may have a Vicat softening temperature above that of the impression material. Upon heating the preform to a temperature that is above the Vicat softening temperature of the impression material polymeric material, the receiving portions may be molded into cavities for receiving the molars. For greater user comfort, the interocclusal appliance formed from said preform lacks substantial polymeric material in front of the user's front teeth. In one alternative embodiment, the appliance lacks polymeric material in contact with the tips of at least some of the user's front teeth. In another alternative embodiment, the user's front teeth are supported by the base with the tips of the user's front teeth in contact with a portion of the top surface of the base. In yet another alternative embodiment, one or more air flow passages are formed through or in the base.

Certain features may be included to help locate the interocclusal appliance formed from the preform in the user's mouth during fitting. For example, the central portion may include a preformed upstanding bridge or arch of impression material between the end portions. In addition, a slanted ledge of impression material may be formed at the central portion. As another example, a front tooth guide may extend generally upwardly from a top surface of the base at the central portion. The front tooth guide may comprise a continuous or discontinuous arcuate ridge, or a series of one or more projections. As yet another example, a pilot channel may be formed in the end portions between inner and outer upstanding ridges that extend generally upwardly from a top surface of the dental arch. It is also possible for the top surface of the base to be concavely dished at the end portions to receive the impression material and form the pilot channel. Moreover, the end portions of the base may be flexed apart. Notches may be cut into the impression material (and/or into the base material) between each end portion and the central portion to assist in flexing the preform.

The interocclusal appliance may have a base with a dental arch of a certain size adapted to fit most adult mouths. However, to accommodate users with larger teeth or a larger dental arch, the preform may include excess impression material bonded at or near the receiving portions in the end portions of the base such that upon fitting the appliance said excess impression material may engage the user's rear teeth that extend beyond the end portions of the base. Such excess impression material will engage the rear teeth that extend beyond the bottom plan surface of the base.

The polymeric material forming the base may have a Shore A hardness of at least about 20. Polymeric material such as ethylene methyl acrylate (EMA) copolymers, acrylics, high density polyethylenes (HDPE), styrenics (IMPS), acrylonitrile-butadiene-styrene (ABS) copolymers, and poly(methylmethacrylates) (IM-PMMA) may be suitable for forming the base. Other FDA-approved polymeric materials may be suitable as well.

One or more types of larger or nanoparticles may be added to the polymeric material forming the base to alter hardness, strength or color of the material forming the appliance. Representative particles include pigments, colorants, plated clays, carbon fibrils and carbon nanotubes.

Particles to impart opacity or translucency to the polymeric material forming the base may serve also as a wear indicator for the interocclusal appliance. As such, a change in color or opacity can evidence that polymeric material is wearing away due to the clenching or bruxing occurring in association with the interocclusal appliance. When a certain color change or opacity variance is observed, the user may determine that the interocclusal appliance is no longer as effective in protecting his or her teeth.

The impression material may comprise ethylene methyl acrylate (EMA) copolymers, ethylene vinyl acetate (EVA) copolymers, acrylics, high density polyethylenes (HDPE), styrenics (IMPS), acrylonitrile-butadiene-styrene (ABS) copolymers, poly(methylmethacrylates) (IM-PMMA), alpha-polyolefins and mixtures thereof. Other FDA-approved polymeric materials may be suitable as well. In one advantageous embodiment, the impression material comprises from 0 to 85% by weight of an ethylene vinyl acetate copolymer having up to about 30% by weight vinyl acetate or mixture of such copolymers, and from 15 to 100% by weight of one or more alpha-polyolefins. If an ethylene vinyl acetate copolymer of mixture of such copolymers is present in the impression material, it may be advantageous to have less than about 10% by weight vinyl acetate. Particles, including larger particles or nanoparticles, may be added to the polymeric material forming the impression material to alter hardness, strength or color of the material forming the appliance.

Some users may prefer an interocclusal appliance that fits over the front teeth rather than the molars. Such an appliance may be formed from a preform comprising a base and an impression material. The base in such embodiment has a bottom plan surface in a configuration of a partial dental arch, and the impression material is bonded to the top surface of said base, with said impression material defining a receiving portion for receiving two or more maxillary front teeth. Just as with the other embodiments noted above, the impression material has a softening temperature lower than the softening temperature of the base so that when the preform is heated the impression material may be softened to take an impression of the user's teeth, such as the front incisors. Preferably, at least six front maxillary teeth are engaged by the impression material to form the interocclusal appliance.

Another aspect of the invention is a method of fabricating an interocclusal appliance for alleviating adverse effects of bruxing or clenching events. In a first embodiment of such method, a one component appliance is formed from a polymeric material having a Shore A hardness of at least 20. In a second embodiment of such method, the one component appliance is formed in a configuration generally of a dental arch having a bottom plan surface and having two end portions and a central portion together forming said dental arch. The end portions each define receiving portions for receiving at least one maxillary molar, and the central portion is shaped so as to be disposed behind at least some of the user's front teeth. The interocclusal appliance formed in this method lacks substantial material in front of the user's front teeth. The method may further include the steps of heating the polymeric material to a temperature that is above its Vicat softening temperature and installing the appliance into a user's mouth and biting pressure is applied thereon so that the receiving portions may be molded into cavities for receiving the maxillary molars. Alternatively, the method may include the step of installing the appliance into a user's mouth and biting pressure is applied thereon so that the receiving portions may be molded into cavities for receiving the maxillary molars, followed by curing the material to retain the shape of the maxillary molar encasement cavities. The polymeric material selected for such methods is consistent with those identified for the interocclusal appliances according to the invention as noted earlier.

In particular variations the method may further comprise the step of indexing the appliance within the user's mouth during the installing step by locating front teeth in front of a slanted ledge formed at the central portion of the dental arch. Or, the method may further comprise the step of indexing the appliance within the user's mouth during the installing step by locating front teeth substantially adjacent to a front tooth guide extending generally upwardly from a top surface of the dental arch at the central portion.

Another alternative method of fabricating an interocclusal appliance for alleviating adverse effects of bruxing or clenching events may comprise forming a two-part preform. The preform has an appliance base of a polymeric material having a Shore A hardness of at least about 20, and an impression material bonded to such base. The impression material may have a Vicat softening temperature lower than the Vicat softening temperature of the material comprising the base. The polymeric material of the appliance base may be ethylene methyl acrylate (EMA) copolymers, acrylics, high density polyethylenes (HDPE), styrenics (IMPS), acrylonitrile-butadiene-styrene (ABS) copolymers, and poly(methylmethacrylates) (IM-PMMA), and mixtures. In one variation the impression material is a polymeric material composition comprising from 0 to 85% by weight of an ethylene vinyl acetate copolymer having up to approximately 30% by weight vinyl acetate, and from 15 to 100% by weight of alpha-polyolefins. Alternatively, the impression material comprises no more than about 25% by weight vinyl acetate. The impression material may consist solely of alpha-polyolefins without ethylene vinyl acetate copolymers.

The polymeric material comprising the base may contain one or more larger particles or nanoparticles, such as for example pigments, colorants, plated clays, carbon fibrils and carbon nanotubes. The polymeric material comprising the impression material may contain one or more larger particles or nanoparticles as well.

The Shore A hardness of the base material may range between about 20 and about 80. The Shore A hardness of the base material may exceed 80.

In another embodiment of this method, the base may be formed in a configuration generally of a dental arch having a bottom plan surface and having two end portions and a central portion together forming said dental arch. The central portion may be shaped so as to be disposed behind at least some of the user's front teeth. The impression material is bonded to the top surface of the base, and the impression material defines receiving portions in the end portions of the base for receiving one or more molars at each end portion. The appliance formed from said base and impression material lacks substantial polymeric material in front of the user's front teeth. The method may further comprise the steps of heating the impression material to a temperature that is above its Vicat softening temperature; and installing the appliance into a user's mouth and applying biting pressure thereon so that the receiving portions may be molded into cavities for receiving the maxillary molars.

In particular variations the method may further comprise the step of indexing the preform within the user's mouth during the installing step by locating front teeth in front of a slanted ledge formed at the central portion of the dental arch. Or, the method may further comprise the step of indexing the preform within the user's mouth during the installing step by locating front teeth substantially adjacent to a front tooth guide extending generally upwardly from a top surface of the dental arch at the central portion.

As another variation, excess impression material may be bonded at or near the receiving portions in the end portion of the base such that upon fitting the preform said excess impression material may engage the user's rear teeth that extend beyond the end portions of the base. The excess impression material engaging the rear teeth extends beyond the bottom surface of the end portions of the base.

Another method of fabricating an interocclusal appliance for alleviating adverse effects of bruxing or clenching events, comprises the steps of forming an appliance base from a polymeric material having a Shore A hardness of at least about 20; and bonding to the base an impression material of a polymeric material composition comprising an ethylene vinyl acetate copolymer having from 0 to 25% by weight vinyl acetate. As one alternative to this method, the Shore A hardness is at least about 80.

BRIEF DESCRIPTION OF THE DRAWINGS

FIG. 1 is a top plan view of a preform for an interocclusal appliance according to a first embodiment of the invention;

FIG. 2 is a front elevational view of the preform of FIG. 1;

FIG. 3 is a side elevational view of the preform of FIG. 1;

FIG. 4 is a right side elevational view in partial cross section, taken along line 4-4 in FIG. 1, showing the interocclusal appliance formed from the preform of the first embodiment fitted within in a user's mouth, with the front incisor tooth extending over the buccal peripheral wall of the appliance;

FIG. 5 is a is a top plan view of a preform of an interocclusal appliance according to a second embodiment of the invention;

FIG. 6 is a front elevational view of the preform of FIG. 5, showing the palate arch provided in such preform;

FIG. 7 is a right side elevational view of the preform of FIG. 5;

FIG. 8 is a cross-sectional view taken along line 8-8 of FIG. 5;

FIG. 9 is a top plan view of a preform of an interocclusal appliance according to a third embodiment of the invention;

FIG. 10 is a front elevational view of the interocclusal appliance formed from the preform of FIG. 9 that is fitted into a user's mouth, with the upper teeth and mouth cavity shown in phantom outline;

FIG. 11 is a right side elevational view of the interocclusal appliance formed from the preform of FIG. 9 fitted into a user's mouth, showing an incisor tooth extending over the buccal peripheral wall of the appliance and supported on a front ledge;

FIG. 12 is a cross-sectional view of the preform taken along line 12-12 of FIG. 9;

FIG. 12A is a front elevational view in partial cross section of a modified interocclusal appliance formed of one material and having a lingual peripheral wall, but lacking the buccal peripheral walls shown in the embodiment of FIG. 9;

FIG. 13 is top plan view of a preform of an interocclusal appliance according to a fourth embodiment of the invention;

FIG. 14 is a front elevational view of the preform of FIG. 13;

FIG. 15 is a bottom plan view of the preform of FIG. 13;

FIG. 16 is a right side elevational view of the preform of FIG. 13;

FIG. 17 is a top plan view of the interocclusal appliance formed from the preform of FIG. 13;

FIG. 18 is a front elevational view of the interocclusal appliance of FIG. 17;

FIG. 19 is a right side elevational view of the interocclusal appliance of FIG. 17;

FIG. 20 is a top plan view of a preform of a fifth embodiment of an interocclusal appliance according to the invention;

FIG. 21 is a front elevational view of the preform of FIG. 20;

FIG. 22 is a left side elevational view of the preform of FIG. 20;

FIG. 23 is a bottom view of the preform of FIG. 20,

FIG. 24 is a cross-sectional view taken along line 24-24 of FIG. 20;

FIG. 25 is a top plan view of the fifth embodiment of an interocclusal appliance formed from the preform of FIG. 20;

FIG. 26 is a front elevational view of the interocclusal appliance of FIG. 25;

FIG. 27 is perspective view of a preform for a sixth embodiment of an interocclusal appliance according to the invention;

FIG. 28 is a perspective view of a preform for a seventh embodiment of an interocclusal appliance according to the invention;

FIG. 29 is a perspective view of a preform for an eighth embodiment of an interocclusal appliance according to the invention;

FIG. 33 is a cross sectional view of an alternative construction of a base with impression material of a preform for an interocclusal appliance in which the base lacks buccal and lingual peripheral side walls and the impression material contacts the top surface of the base;

FIG. 34 is a cross-sectional view of an alternative construction of a base with impression material of a preform for an interocclusal appliance in which the base has a concavely curved top surface and the impression material contacts the top surface of the base;

FIG. 35 is a cross-sectional view of the preform of FIG. 31, which has a base having buccal and lingual peripheral side walls and a top surface and impression material is held on the top surface in the space between the side walls; and FIG. 36 is a front elevational view of a modification to the eighth embodiment of the interocclucal appliance according to the invention which incorporates breathing enhancing bores.

DESCRIPTION OF THE PREFERRED EMBODIMENTS

Figure 31:
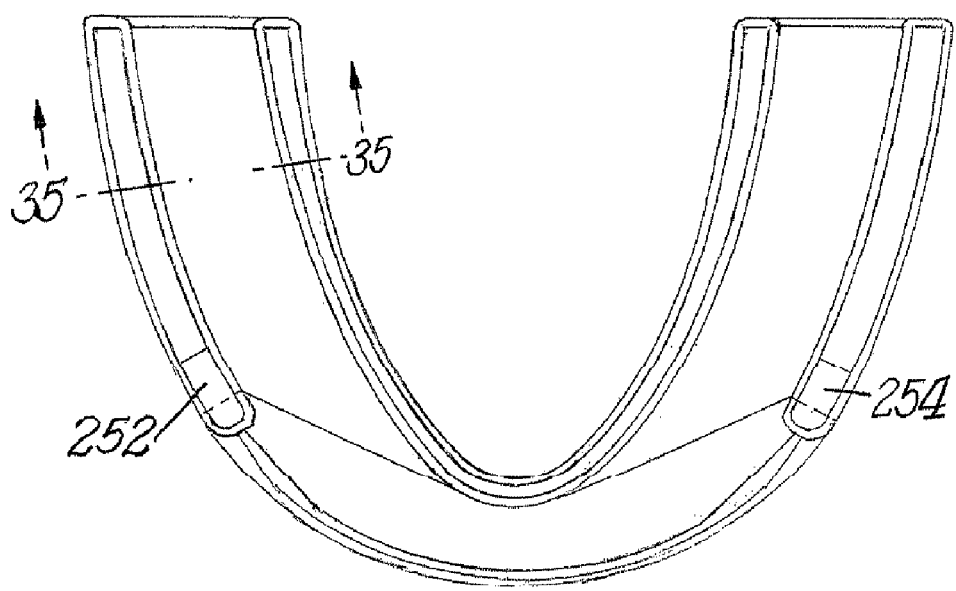
FIG. 31 is a top plan view of the preform of FIG. 29.

Referring first to FIGS. 1-3, a first embodiment of a preform 10 for an interocclusal appliance 42 is shown. The preform 10 has a base 12 or bite plate with a top surface and a bottom surface. An impression material 14 is bonded or adhered onto the top surface of the base 12. One preferred bonding is by molding the impression material over the base. The base 12 may be formed by injection molding a thermoplastic resin into a base mold cavity, and this base 12 is then placed into an occlusal appliance mold cavity. The impression material 14 may be injected into the occlusal appliance mold cavity over the base 12. The mold bond between the base 12 and the impression material 14 (which later is transformed into the maxillary encasement) is required to withstand the lateral and compressive stresses encountered during bruxing or clenching at oral cavity temperatures.

The base 12 is in the form of a maxillary dental arch, having an end portion 16 at one terminus of said arch and another end portion 18 at the other terminus of said arch. Between the two end portions 16, 18 is a central portion 20 of the base. Preferably, and the bottom surface (or occlusal face) of the base is generally planar. The buccal sidewalls of the base 12 may slope downwardly from the rear of the preform 10 to the labial face at the central portion 20 as shown in FIG. 3. The thickness of the base material may range from about 0.25 mm to about 4.0 mm.

The impression material 14 generally covers the top surface of the base 12. The impression material 14 is formed to have a first outer upstanding ridge 22 and a second outer upstanding ridge 24, and an inner upstanding ridge 26. Optionally, a step 28 is formed in the inner upstanding ridge 26 such that the inner upstanding ridge of impression material at the central portion 20 of the base is higher than the inner upstanding ridge of impression material formed at the end portions 16, 18 of the base 12. The upper surfaces of the impression material between the outer upstanding ridges 22, 24 (buccal peripheral walls) and the inner upstanding ridge 26 (lingual peripheral wall) define tooth receiving portions 30, 32. Tooth receiving portions 30, 32 may alternately be called pilot channels configured to facilitate placement of the user's maxillary molars at an optimal position during and throughout self-fitting of the appliance. The front face 34 of the inner upstanding ridge 26 is sloped downwardly, at an angle complementary to the angle at which upper or maxillary front incisor and/or bicuspid teeth generally are disposed in an adult mouth. The impression material 14 is transformed into a maxillary molar encasement during self-fitting of the interocclusal appliance 42 (FIG. 4). Preferably, to secure a desired maxillary molar encasement, about 3.5 g to about 7.0 g of impression material covers the base material. However, more or less impression material may be used to form the preform as desired.

An interocclusal appliance 42 (FIG. 4) of a first embodiment of the invention is formed from the preform 10 of FIGS. 1-3. The preform 10 is heated, such as by immersion in boiling water for 30 seconds to 2 minutes to soften the impression material 14. The preform 10 is heated to a temperature that can be comfortably withstood by oral tissue (e.g., preferably below about 140° F.). The preform 10 is then inserted into the mouth (oral cavity) with the upper molars (maxillary occlusal surfaces) seated in the teeth receiving portions 30, 32 of the preform 10. Biting pressure is applied and the maxillary molars are impressed into the impression material 14. The impression material flows over and around the molars to adapt to the shape of the surfaces of the maxillary molars. Upon cooling, the impression material 14 is transformed into a reusable flexible maxillary molar encasement within the appliance 42.

Alternatively, depending upon polymeric material selected as the impression material, the interocclusal appliance 42 may be fitted first and then heated to set the polymeric material. In this case, before heating, preform 10 is inserted into the mouth (oral cavity) with the upper molars (maxillary occlusal surfaces) seated in the teeth receiving portions 30, 32. Biting pressure is applied and the maxillary molars are impressed into the impression material 14. The preform 10 is then heated, such as by immersion in boiling water for a desired time so as to set the polymeric material into a reusable flexible maxillary molar encasement within the appliance 42.

Referring back to FIG. 1, fitting of the preform 10 is simplified where the preform 10 flexes. By flexing it is meant that the end portions 16, 18 can be separated from one another a greater distance by urging end portion 18 away from end portion 16. Thus, as shown in FIG. 1, end portions 16, 18 are separated from one another initially by a first distance, which can be represented by the distance L1 from center line C. Upon flexing, end portions 16, 18 are separated from one another by a second distance, which is represented in FIG. 1 by the distance L2 from the center line C, where L2 is greater than L1. For example, the range of flex distance (L2-L1) may be from about 2 to 35 mm. Even though the material selected for the base 12 is not expected to be softened upon heating during the fitting procedure, the configuration of the preform 10 with a base central portion 20 narrower in width than the widths of the end portions 16, 18 permits greater flexing and correspondingly greater ease when fitting the appliance over maxillary molars.

While the impression material 14 in the teeth receiving portions 30, 32 adapts to the shape of the surfaces of the maxillary molars, the upstanding ridge 26 may be lengthened and fitted to the user's palate tissue extending behind the front teeth. Referring to FIG. 4, the appliance 42 has been fitted in a mouth 38 so that the upstanding ridge of the preform is stretched and thinned to form a flap or palate molded surface 44. Thus, although FIG. 4 is identified as a partial cross-section of the preform in FIG. 1, more accurately, it is a partial cross-section of the appliance 42 formed from the preform of FIG. 1. The impression material forming the front portion of the upstanding ridge 26 including the step 28 in such ridge 26 has been shaped to conform to the user's palate and to support the user's front teeth when the appliance 42 is worn.

FIG. 4 also shows that the interocclusal appliance 42 fits in the user's mouth 38 such that the sloped front face 34 of the preform 10 now contacts the back surface of the user's front teeth 40. No impression material 14 contacts the front surface of the user's front teeth. No impression material extends between the front teeth and the user's upper lip. No impression material and no base material extend below the lower tip of the user's front teeth. As so fitted, the interocclusal appliance leaves a more natural gap between a user's front incisor teeth. Such gap or air channel permits the user to breathe more naturally through his or her mouth during sleep.

For embodiments in which the impression material is heated before fitting to the teeth, rheological characteristics of the base polymeric material (often a thermoplastic material, but may be a thermoset material) include a Vicat softening temperature (ASTM D1525) of at least 65° C., which is well above the temperatures reached during the fitting procedure, and a Shore A hardness of at least about 20. One range for Shore A hardness for base materials is from about 20 to about 80 (e.g., 19 to 78). The polymeric material selected for the base has a softening temperature sufficiently above that of the polymeric material selected for the impression material such that the thickness of the base is not significantly reduced as a result of compressive forces during fitting. The base material must not be toxic to humans when incorporated into an interocclusal appliance for oral use.

Polymeric materials, including resins, meeting these criteria include, but are not limited to, ethylene methyl acrylate (EMA) copolymers, acrylics, high density polyethylenes (HDPE), styrenics (IMPS), acrylonitrile-butadiene-styrene (ABS) copolymers, poly(methylmethacrylates) (IM-PMMA), polypropylene, polycarbonate, polycaprolactam, polycaprolactone, polyurethanes, polyesters, polypropylene ethylene propylene diene monomer (PP/EPDM), thermoplastic vulcanizates (TPV), acrylic rubber TPV, styrene-butadiene-styrene (SBS) TPV, low density polyethylene (LDPE), polyvinylchloride (PVC), very low density polyethylene (VLDPE), styrene-butadiene copolymer (SBC) elastomer compounds, styrene-butadiene-styrene (SBS) linear block copolymers, styrene-isoprene-styrene (SIS) linear block copolymers, styrene-butadiene (SB)n branched copolymers, styrene-co-ethylene-butene-styrene (SEBS) linear block copolymers, styrene-co-ethylene-propylene (SEP) diblock copolymers, styrene-co-ethylene-ethylene-propylene-styrene (SEEPS) copolymers, mineral reinforced thermoplastic ethylene-styrene (TES/SEBS) polyethersulfone (PES), glass reinforced polyethersulfone, polyphenylsulfone (PPSU), styrene-acrylonitrile (SAN), acrylic-styrene-methyimethacrylate coplyomers (NAS), polydimethylsilicone (PDMS), polyurea, silicone-polyurea, segmented polyurethane (SPU), perfluoroelastomer (FFKM), perfluoroelastomer (FEPM), chlorosulfonated polyethylene rubber, fluoroelastomer, silicone room temperature vulcanizate (RTV), cast polyurethane, chloroprene rubber, hydrogenated nitrile-butadiene rubber (HNBR), nitrile rubber, silicone rubber, perfuoroelastomer compounds (FFKT), and mixtures thereof.

An exemplary thermoplastic material suitable for the base is an ethylene methyl acrylate (EMA) copolymer available from DuPont under the trademark ELVALOY®1609 AC. This EMA copolymer contains approximately 9% by weight acrylate and has a Vicat softening temperature of 70° C., and a Shore A hardness of 97. Another thermoplastic material that may be used for the base is ELVALOY® EMA copolymer blended with ELVAX® EVA ethylene vinyl acetate copolymer or with PELLETHANE® TPU elastomer, such as in proportion ranging between 10% to 50% PELLETHANE TPU by weight. PELLETHANE® 2103-80 AEN is a thermoplastic polyurethane elastomer available from Dow Chemical Co. Yet another thermoplastic material that may be used for the base is ELVAX 750 EVA blended with LLDPE or LDPE with the LLDPE or LDPE content ranging from 25% to 90% by weight.

Other exemplary thermoplastic materials suitable for the base are Cyro Acrlitei SuPure M30 acrylic available from Cyro Industries, Nova Sclair 2908 high density polyethylene (HDPE) available from Nova Chemicals, Nova Chemicals NAS 30 Series High Performance Styrenic, and BASF Terlux 2812 acrylonitrile-butadiene-styrene copolymer. Table 1 below identifies characteristics of certain of these exemplary polymeric materials. Such materials are indicated as FDA-approved for oral use.

TABLE 1

| Property/Polymer Bottom Material | Flex Mod (Gpa) | Durometer, D, M, R | Notched Izod (J/cm) | Haze % | FDA 21 CFR | Linear Shrink (cm/cm) |
|---|---|---|---|---|---|---|
| Elvaloy 1609 | 0.80 | 46 D | NV-Med | NV-Med | Yes 177.1520(b) | NV |
| Acrylic | 3-3.3 | 90-94 M | 0.25 | 1.0 | Yes | NV |
| High Density Polyethylene (HDPE) | 0.80-1.28 | 55-69 D 60 R <55M | 0.2-0.8 | NV-High | Yes 177.1520(c) 2.2 | NV |
| Poly(propylene) (h-PP, co-PP) | 1.37 | 108 R | 0.3 | NV-High | Yes | |
| Styrenics (IMPS, PS) | 2-3.3 | 70-74 M | 0.2-1.27 | 0.6-1.0 | Yes Class VI | 0.002-0.006 |
| Polyesters (PET, PBT) | 1.7-4.1 | 72-93 M | 0.27-NB | NV-Low | Yes | |
| Injection Molded Poly(methylmethacrylate) (PMMA, IM-PMMA) | 2.6-3.1 | 68-89 M | 0.12-0.3 | 1-2 | Yes 177.1010; 180.22; 1580 | 0.002-0.006 |
| Poly(carbonate) (PC) | 1.8-4.1 | 65 M 118 R | 16-21 | 1-2 | Yes | |
| Poly(caprolactam) Nylon 6 | 0.1-3.2 | 55-88 M | 0.7-NB | NV-High | Yes | |
| Acrylonitrile-butadiene-styrene co-polymer (ABS) | 2.65 | 60 M | 1.25 | NV-Med | Yes Class IV | 0.4-0.7 (in/in) |

NV = No value
NB = No break

Suitable polymeric materials for the impression material 14 include thermosetting and thermoplastic polymer resins. Potential polymeric materials for the impression material include ethylene methyl acrylate (EMA) copolymers, ethylene vinyl acetate (EVA) copolymers, acrylics, high density polyethylenes (HDPE), styrenics (IMPS), acrylonitrile-butadiene-styrene (ABS) copolymers, poly(methylmethacrylates) (IM-PMMA), alpha-polyolefins, polypropylene-ethylene propylene diene monomer (PP/EPDM) thermoplastic vulcanizates (TPV), acrylic rubber TPV, styrene-butadiene-styrene (SBS) TPV, low density polyethylene (LDPE), polyvinylchoride (PVC), styrene-butadiene copolymer (SBC) elastomer compounds, styrene-butadiene-styrene (SBS) linear block copolymers, styrene-isoprene-styrene (SIS) linear block copolymers, styrene-butadiene (SB)n branched copolymers, styrene-co-ethylene-butene-styrene (SEBS) linear block copolymers, styrene-co-ethylene-propylene (SEP) diblock copolymers, styrene-co-ethylene-ethylene-propylene-styrene (SEEPS) copolymers, mineral reinforced thermoplastic ethylene-styrene (TES/SEBS), styrene-acrylonitrile (SAN), polydimethylsilicone (PDMS), polyurea, silicone-polyurea, segmented polyurethanes (SPU), perfluoroelastomer (FFKM), perfluoroelastomer (FEPM), chlorosulfonated polyethylene rubber, fluoroelastomer, silicone room temperature vulcanizate (RTV), cast polyurethane, chloroprene rubber, hydrogenated nitrile-butadiene rubber (HNBR), nitrile rubber, silicone rubber, perfuoroelastomer compounds (FFKT), and mixtures thereof.

Such polymeric materials for the impression material may include an ethylene vinyl acetate (EVA) copolymer available from DuPont under the trademark ELVAX® having a vinyl acetate content of at least 25%. One preferred EVA copolymer is ELVAX® 150 having a 33% vinyl acetate content by weight, a Vicat softening temperature of 36° C., and a Shore A hardness of 73. Alternatively, the impression material may be an alpha-polyolefin, such as EXACT 4006 available from ExxonMobil, ENGAGE 8407 and ENGAGE 8842 available from Dow Chemical or AFFINITY EG 8200G available from Dow Chemical. The polymeric material for the impression material may be a mixture of resins, such as from 10 to 100% by weight alpha-polyolefin with from 0 to 90% by weight of an ethylene vinyl acetate copolymer having up to about 30% by weight vinyl acetate. Alternatively, such mixture may be from 15 to 100% by weight alpha polyolefin with from 0 to 85% by weight of an ethylene vinyl acetate copolymer having up to about 30% by weight vinyl acetate. Table 2 below sets out characteristics of certain of these exemplary polymeric materials. Such materials are indicated as FDA-approved for oral use.

TABLE 2

| Property/ Polymer-Impression Material | Vicat Soften Pt, C./F. | Durometer A | Durometer D | Melting Pt, C./F. | FDA 21 CFR |
|---|---|---|---|---|---|
| Elvax 150 | 36/97 | 73 | 24 | 63/145 | 177.1350 (a)(1) |
| Exact 4006 | 43/109 | 79 | 20 | 60/140 | 175.105 (a)(2) |
| Engage 8407 | 41 | 72 | 20 | 60 | 177.1520(c) 3.2c |
| Engage 8842 | CNA | 54 | 11 | 38 | 177.1520(c) 3.2c |
| Affinity EG 8200G | <45/<113 | 70 | NV | 63/145 | 176.170(c) |

NV = No value
CNA = Can not Ascertain

Particles, including larger particles or nanoparticles may be added to the polymeric materials forming the base or the impression material. For example, colorants (such as pigments known for use with thermoplastic and thermoset resins) may be incorporated into the base or impression material to improve aesthetics. Colorants may have added benefit to serve as a wear indicator, so that the user can detect when portions of the base material are wearing down due to bruxing or clenching after an appliance is worn. As another example, plated clays, carbon fibrils and/or carbon nanotubes may be added to enhance strength of the base material or the impression material.

Referring next to FIGS. 5 to 8, a second embodiment of the invention comprises a preform 50 having a base 52 or bite plate with a top surface and a bottom surface. An impression material 54 is adhered or bonded onto the top surface of the base 52, such as by co-molding. The base 52 has two end portions 56, 58 that are joined by an arch 60 formed between the two end portions 56, 58. Arch 60 curves concavely such that each bottom tip of said arch meets an end portion the bottom surfaces (or occlusal faces) of the end portions 56, 58 of the base are generally planar. The buccal sidewalls of the end portions of the base 12 may slope downwardly slightly from the rear of the preform 50 toward the front of the preform as shown in FIG. 7.

By virtue of flexibility of the arch 60 material, the preform 50 may be flexed from a first position where end portions 56, 58 are spaced apart a first distance to a second position where end portions 56, 58 are spaced apart a second distance, where the second distance is greater than the first distance. Notches 62, 64 are formed in the base 52 where each bottom tip of said arch 60 meets an end portion 56, 58. Notches 62, 64 enhance the ability to flex the preform 50 from a first position where end portions 56, 58 are spaced apart a first distance to a second position where end portions 56, 58 are spaced apart a second distance, where the second distance is greater than the first distance. Such flexing is not shown in FIG. 5.

The impression material 54 generally covers the top surface of the base 52. The impression material 54 is formed to have a first outer upstanding ridge 66 and a second outer upstanding ridge 68, and an inner upstanding ridge 70 that extends from arch 60. The upper surfaces of the impression material between the outer upstanding ridges 66, 68 (buccal peripheral walls) and the inner upstanding ridge 70 (lingual peripheral wall) define tooth receiving portions 72, 74. Tooth receiving portions 72, 74 may alternately be called pilot channels configured to facilitate placement of the user's maxillary molars at an optimal position during and throughout self-fitting of the appliance. The top face of the arch 60 is sloped downwardly, at an angle complementary to the angle of a palate in an adult mouth. The impression material 54 at the teeth receiving portions 72, 74 is transformed into a maxillary molar encasement during self-fitting of the interocclusal appliance of this second embodiment. In addition, the arch 60, which aids in self-fitting the interocclusal appliance in the mouth, may be stretched and thinned to conform to the palate surface behind the front maxillary teeth when the impression material 54 is softened for self-fitting the appliance.

A finished appliance according to this second embodiment is not shown in the Figures. However, just as with the first embodiment shown in FIG. 4, for this second embodiment of interocclusal appliance, no impression material 54 contacts the front surface of the user's front teeth. No impression material extends between the front teeth and the user's upper lip. No impression material and no base material extend below the lower tip of the user's front teeth. The front teeth are supported by the impression material from behind, but are not encased in impression material, and thus the interocclusal appliance is more comfortable to wear.

FIGS. 9 to 12 show a preform 80 and an interocclusal appliance 110 for a third embodiment of the invention (appliance 110 shown in FIG. 11). The preform 80 has a base 82 and impression material 84 molded to a top surface of such base 82. The base 82 is in the shape of a maxillary dental arch, having end portions 86, 88 and a central portion 90 between such end portions 86, 88. The end portions 86, 88 have upstanding side walls 87, 89 and an upstanding lingual wail 91 that extends along the dental arch along the end portions 86, 88 and the central portion 90. The central portion 90 of the base 82 has only the upstanding lingual wall 91, and does not have an upstanding labial or front wall.

The impression material 84 generally covers the top surface of the base 82. The impression material 84 is formed to have a first outer upstanding ridge 92 and a second outer upstanding ridge 94, and an inner upstanding ridge 96. Optionally, a step (not shown) may be formed in the inner upstanding ridge 96 such that the inner upstanding ridge of impression material at the central portion 90 of the base is higher than the inner upstanding ridge of impression material formed at the end portions 86, 88 of the base 82. The upper surfaces of the impression material between the outer upstanding ridges 92, 94 (buccal peripheral walls) and the inner upstanding ridge 96 (lingual peripheral wall) define tooth receiving portions 98, 100. Tooth receiving portions 98, 100 may alternately be called pilot channels configured to facilitate placement of the user's maxillary molars at an optimal position during and throughout self-fitting of the appliance. The front face 102 of the inner upstanding ridge 96 is sloped downwardly, at an angle complementary to the angle at which upper or maxillary front incisor and/or bicuspid teeth generally are disposed in an adult mouth. The impression material 84 is transformed into a maxillary molar encasement during self-fitting of the interocclusal appliance 110 (FIG. 11).

While the impression material 84 in the teeth receiving portions 98, 100 adapts to the shape of the surfaces of the maxillary molars, the upstanding ridge 96 may be lengthened and fitted to the user's palate tissue extending behind the front teeth 104. Referring to FIG. 11, the appliance 110 has been fitted in a mouth 106 so that the upstanding ridge of the preform is stretched and thinned to form a flap or palate molded surface 112.

FIG. 11 also shows that the interocclusal appliance 110 fits in the user's mouth 106 such that the sloped front face 102 of the impression material contacts the back surface of the user's front teeth 104 to support those teeth as the appliance is worn. The top surface of the base 82 contacts the lower tips of the user's front teeth. As illustrated in FIG. 11, no impression material 84 contacts the front surfaces of the user's front teeth. No impression material extends between the front teeth and the user's upper lip. Thus, this third embodiment is comparable to the first embodiment shown in FIG. 4, except that base material extends below the lower tips of the user's front teeth 104 to support those teeth when the appliance is worn. In this manner, base material or bite plate separates occlusal surfaces of all of the user's teeth, not just the molars.

While the first 10, second 50 and third 80 embodiments of the preforms according to the invention have been shown optimally without any impression material extending between the front surfaces of the user's front teeth and the user's upper lip, some impression material may contact the user's front teeth in finished appliances within the scope of the invention. Not all users will have complete sets of front teeth, and not all users will have dental arches that match the span of the dental arch of the preform. Thus, it is intended that appliances formed from preforms that do not have substantial impression material extending in front of a user's front teeth are within the scope of the present invention. Unlike prior self-fitted interocclusal appliances, to achieve the comfortable fit desired herein, the appliances according to the invention are not intended to have substantial impression material or base material in front of a user's teeth, or in contact with a user's front (labial) gum tissue.

A fourth embodiment of a preform 120 for an interocclusal appliance 140 (appliance 140 shown in FIGS. 17 to 19) is shown in FIGS. 13 to 16. The preform 120 has a first base portion 122 and a second base portion 123. The base portions form bite plates with generally smooth and planar bottom surfaces and with top surfaces designed to receive impression material. The top surfaces have front edges and rear edges.

Impression material 124 is bonded or attached (such as by molding) to the top surfaces of the base portions 122, 123. As shown in FIGS. 13 to 16, the impression material 124 has a right side molded to the first base portion 122 and a left side molded to the second base portion 123. The right and left sides are joined together by a bridge 130 of impression material 124. The right side and left side have outer upstanding ridges 132 and inner upstanding ridges 134 defining tooth receiving portions 136 and 138. Bridge 130 is shown in FIGS. 13 and 15 as being centrally disposed between base portions 122 and 123. It is also conceivable that such bridge 130 may be positioned closer to the rear edges of the base portions 122, 123. Shifting the location of bridge 130 of impression material 124 may enhance fitting of the appliance into a user's mouth by making a more comfortable engagement with the user's palate (as described in more detail below).

For embodiments in which a heat and fit procedure is used, upon heating preform 120, impression material 124 is softened. The preform 120 is then installed in the user's mouth with the maxillary molars in contact with the tooth receiving portions 136, 138. The softer impression material forming the bridge 130 in the preform 120 enables the user to flex the first and second base portions 122, 123 closer to or farther from one another during fitting. Upon applying biting pressure, impressions or indentations of left side and right side molars 144, 146 are made in the impression material 124. During the fitting procedure, the impression material forming bridge 130 is also softened such that bridge 130 may be shaped into a palate arch 142 to conform to the contour of the user's palate. Accordingly, an interocclusal appliance 140 (FIGS. 17 to 19) comfortably shapes to fit the bite surfaces of the maxillary molars, with a palate arch 142 to help maintain the appliance in register within the user's mouth. No impression material or base material is in contact with the user's front teeth. No impression material or base material is present between the user's front lip and front teeth.

Referring next to FIGS. 20 to 24, a fifth embodiment of a preform 150 for an interocclusal appliance 160 (appliance 160 shown in FIGS. 25 and 26) is shown. The preform 150 has a base 152 to which is bonded or adhered (such as by molding) an impression material 154. The base 152 forms an arc shape comparable to the maxillary arch or mandibular arch of the front teeth in an adult mouth, with a pair of parallel curved front and rear walls and two end walls. The base 152 has a front labial ridge 156 upstanding from the top surface of the base. Preferably, the front labial ridge 156 extends along the entire front wall or labial edge of the base 152. The base 152 has a generally smooth and planar bottom surface for occlusal contact between front teeth.

Impression material 154 is bonded or molded to the top surface of the base 152. Impression material 154 follows the dental arch contour of the base 152. The top surface of the impression material 154 comprises tooth receiving portion 158.

When using a heat and fit procedure, an interocclusal appliance 160 is formed upon heating the preform 150 to soften the impression material 154 without substantially softening the base material. The preform 150 is then inserted into the mouth such that the impression material is in contact with the tips of the user's front teeth. Biting pressure is applied to imbed either the maxillary front teeth or the mandibular front teeth into the impression material 154. The front labial ridge 156 of the base 152 helps to seat the teeth in proper register during the fitting procedure.

A portion of the impression material 154 takes impression of the user's front teeth. Tooth indentations 162 are thus formed in the interocclusal appliance 160 (see FIG. 25). Preferably, impressions or indentations 162 are formed for at least six front maxillary teeth, such as incisors and bicuspids. In FIG. 25, the appliance 160 has impressions or indentations 162 for eight front teeth.

During the fitting procedure for an appliance to be worn over the maxillary front teeth, the user may shape the impression material 164 of the preform 150 to create a lingual lip or palate-contoured raised flap 164 that helps to engage the appliance 160 and register it in suitable position in the user's mouth. The palate contoured raised flap 164 may be formed by pressing the softened impression material 154 with the tongue or with fingers or thumbs while preform with softened impression material 154 is held within the mouth.

Concurrently, as the dental impressions or indentations 162 are formed in the impression material 154, the impression material may form a raised or upstanding front (labial) lip 166. In this way the interocclusal appliance 160 contacts the front and rear Surfaces of the user's front teeth, with the base 152 disposed under the tips of such teeth.

The interocclusal appliance 160 of FIGS. 25 and 26 is different from the other appliance embodiments described previously herein in that no base material or impression material encases the maxillary or mandibular molars. The appliance 160 separates the upper and lower teeth by spacing apart the front teeth, rather than by spacing apart the back teeth or molars. Still, such embodiment is more comfortable than prior self-fitting interocclusal appliances because the front teeth (incisors and bicuspids) are supported at the rear and no substantial impression material contacts the user's upper front gums.

Referring next to FIG. 27, a sixth embodiment of a preform 180 for an interocclusal appliance is shown. The preform 180 has a base 182 or bite plate with a top surface and a bottom surface. An impression material 184 is bonded or adhered (such as by molding) onto the top surface of the base 182. The base 182 may be formed by injection molding a thermoplastic resin into a base mold cavity, and this base 182 is then placed into an occlusal appliance mold cavity. The impression material 184 may be injected into the occlusal appliance mold cavity over the base 182. The mold bond between the base 182 and the impression material 184 (which later is transformed into the maxillary or mandibular encasement) is required to withstand the lateral and compressive stresses encountered during bruxing or clenching at oral cavity temperatures.

The base 182 is in the form of a maxillary or mandibular dental arch, having an end portion 186 at one terminus of said arch and another end portion 188 at the other terminus of said arch. Between the two end portions 186, 188 is a central portion 190 of the base. Preferably, and the bottom surface (or occlusal face) of the base is generally planar The buccal sidewalls of the base 182 may slope slightly downwardly from the rear of the preform 180 to the labial face at the central portion 190. The thickness of the base material may range from about 0.25 mm to about 4.0 mm.

The impression material 184 generally covers the top surface of the base 182. The impression material 184 is formed to have a first outer upstanding ridge 192 (buccal peripheral wall) and a second outer upstanding ridge 194 (buccal peripheral wall), and an inner upstanding ridge 196 (lingual peripheral wall). The upper surfaces of the impression material between the outer upstanding ridges 192, 194 (buccal peripheral walls) and the inner upstanding ridge 196 (lingual peripheral wall) define tooth receiving portions 198, 200. Tooth receiving portions 198, 200 may alternately be called pilot channels configured to facilitate placement of the user's maxillary or mandibular molars at an optimal position during and throughout self-fitting of the appliance. A front ledge 202 formed in the impression material 184 at the center portion 190 is sloped downwardly. For an appliance to be worn over upper teeth, this slope may be at an angle complementary to the angle at which upper or maxillary front incisor and/or bicuspid teeth generally are disposed in an adult mouth. The impression material 184 is transformed into either a maxillary molar encasement or mandibular molar encasement during self-fitting of the interocclusal appliance.

A heat and fit self-fitting procedure may be used to form an interocclusal appliance of the sixth embodiment of the invention from the preform 180 of FIG. 27 for wearing over the maxillary (upper) teeth. First, the preform 180 is heated, such as by immersion in boiling water for 30 seconds to 2 minutes to soften the impression material 184. The preform 180 is heated to a temperature that can be comfortably withstood by oral tissue, such as a temperature between about 110° F. and 140° F. The preform 180 is then inserted into the mouth (oral cavity) with the upper molars (maxillary occlusal surfaces) seated in the teeth receiving portions 198, 200 of the preform 180. Biting pressure is applied and the maxillary molars are impressed into the impression material 184. The impression material flows over and around the molars to adapt to the shape of the surfaces of the maxillary molars. Concurrently, the impression material 184 at the ledge 202 and the impression material forming the central portion of the inner ridge 196 may be shaped to conform to a portion of the user's palate behind the front teeth. Upon cooling, the impression material 184 is transformed into a reusable flexible maxillary molar encasement within the appliance. No impression material 184 or only an insubstantial amount of impression material contacts the front surface of the user's front teeth. No substantial impression material extends between the front teeth and the user's upper lip. No impression material and no base material extend below the lower tips of the user's front teeth. (Alternatively, the base material may extend below the lower tips of the user's front teeth for extra support.) As so fitted, the interocclusal appliance of this sixth embodiment leaves a more natural gap between a user's front incisor teeth. Such gap or air channel permits the user to breathe more naturally through his or her mouth during sleep.

Referring next to FIG. 28, a seventh embodiment of the invention comprises a preform 210 having a base 212 or bite plate with a top surface and a bottom surface. An impression material 214 is bonded or adhered onto the top surface of the base 212. The base 212 has two end portions 216, 218 that are joined by a center portion 220 formed between the two end portions 216, 218. The bottom surfaces (or occlusal faces) of the end portions 216, 218 of the base are generally planar. The buccal sidewalls of the end portions of the base 212 may slope downwardly from the rear of the preform 220 toward the front of the preform.

Because the center portion 220 has a shorter width in cross-section than the end portions 216, 218. The preform 220 has ability to flex, comparable to the embodiment shown in FIG. 1. The preform 220 may be flexed from a first position where end portions 216, 218 are spaced apart a first distance to a second position where end portions 216, 218 are spaced apart a second distance, where the second distance is greater than the first distance.

In the embodiment in FIG. 28, the impression material 214 generally covers the top surface of the base 212. The impression material 214 is formed to have a first outer upstanding ridge 222 and a second outer upstanding ridge 224, and an inner upstanding ridge 226 (lingual peripheral wall) in the form of an arc. A raised step 227 is formed at the center portion of the upstanding ridge 226. The upper surfaces of the impression material between the outer upstanding ridges 222, 224 (buccal peripheral walls) and the inner upstanding ridge 226 (lingual peripheral wall) define tooth receiving portions 228, 230. Tooth receiving portions 228, 230 may alternately be called pilot channels configured to facilitate placement of the user's maxillary molars (or mandibular molars) at an optimal position during and throughout self-fitting of the appliance. The impression material 214 at the teeth receiving portions 228, 230 is transformed into a maxillary molar encasement (or alternatively mandibular molar encasement) during self-fitting of the interocclusal appliance of this seventh embodiment.

The impression material 214 of the preform 220 also is formed to have a downwardly sloped front face 232 at the central portion 220. This downwardly sloped front face 232 helps to register and seat the preform in the user's mouth behind the front teeth. The downwardly sloped front face 232 may be shaped to conform to a portion of the user's palate behind the front teeth during the self-fitting procedure. Just as with the embodiment of FIGS. 1-4, if a heat and fit self-fitting procedure is used, the preform 220 is heated, such as by immersion in hot water, to soften the impression material 214 before the preform 220 is inserted over the teeth of the user's maxillary arch to transform into a maxillary molar encasement. Alternatively, the heated preform 220 may be inserted over the teeth of the user's mandibular arch to transform into a mandibular molar encasement.

A finished appliance according to this seventh embodiment is not shown in the Figures. However, just as with the first embodiment shown in FIG. 4, for this seventh embodiment of interocclusal appliance, no substantial impression material 214 contacts the front surface of the user's front teeth. No substantial impression material extends between the front teeth and the user's upper lip. No impression material and no base material extend below the lower tip of the user's front teeth. The front teeth are not encased in impression material, and thus the interocclusal appliance is more comfortable to wear.

Figure 30:
FIG. 30 is a front elevational view of the preform of FIG. 29.
Figure 32:
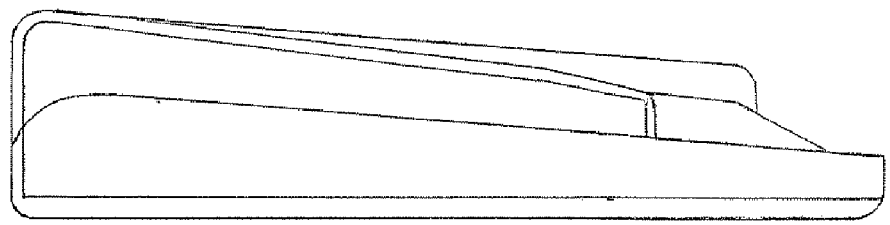
FIG. 32 is a left side elevational view of the preform of FIG. 29.

An eighth embodiment of the invention shown in FIGS. 29 to 32 and 35 comprises a preform 240 having a base 242 or bite plate in the form of a dental arch and having a top surface and a bottom surface. An impression material 244 is bonded or adhered onto the top surface of the base 242. The base 242 has two end portions 241, 243 that are joined by a center portion 249 formed between the two end portions 241, 243. The bottom surfaces (or occlusal faces) of the end portions 241, 243 of the base are generally planar and slope downwardly toward the center portion 249 of the arch forming the base 242. The buccal sidewalls of the end portions 241, 243 of the base 242 may slope downwardly from the rear of the preform 240 toward the front of the preform as shown best in FIG. 32.

The impression material 244 generally covers the top surface of the base 242. Extra impression material 244 may extend beyond the end portions 241, 243 of the base 242. Preferably, about 3.5 g to about 7.0 g of impression material are included in the preform according to this embodiment shown in FIG. 29 to ensure sufficient molar encasement. The impression material 244 is formed to have a first outer upstanding ridge 246 and a second outer upstanding ridge 247, and an inner upstanding ridge 248 (lingual peripheral wall) in the form of an arc. The impression material 244 follows the slope contour of the base 242, and the top surface of the outer upstanding ridges 246, 247 may slope at the same angle or at a different angle from the slope of the base 242. At the front ends 256, 258 of the outer upstanding ridges 246, 247 the slope of the top surface of the impression material may change to a steeper angle than at the end or mid point of such ridges. In addition, at the center portion of the arc of the base 242, the top surface of the impression material 244 more steeply slopes downwardly forming a ledge 250. Such slanted front ledge 250 facilitates fitting the preform into the user's mouth when self-fitting to form an interocclusal appliance as explained in more detail below.

The impression material ledge 250 terminates at the apex portion of the arch of the base 242. Thus, a portion of the top surface of the base 242 at the apex portion of the arc or arch is exposed without impression material 244 thereon. At that apex portion of the arc, a ridge 260 extends slightly upwardly from the top surface of the base 242. Such ridge 260 facilitates seating the preform 240 into a user's mouth when fitting the interocclusal appliance as explained in more detail below. While illustrated as a continuous upstanding ridge in FIGS. 29-32, a guide to facilitate seating the preform 240 into a user's mouth alternatively may be a single raised portion or a series of raised portions, such as nibs or burrs, or a discontinuous ridge, such as a series of raised dashes.

The ridge 260 and the surface of the base 242 have a greater surface area exposed without impression material in the space adjacent to the front ends 256, 258 of the outer upstanding ridges 246, 247. Such base top surface without impression material facilitates positioning the preform 240 into a user's mouth and conforming the impression material to the teeth and palate surfaces when fitting the interocclusal appliance as explained in more detail below.

The upper surfaces of the impression material between the outer upstanding ridges 246, 247 (buccal peripheral walls) and the inner upstanding ridge 248 (lingual peripheral wall) define tooth receiving portions 252, 264. Tooth receiving portions 262, 254 may alternately be called pilot channels configured to facilitate placement of the user's maxillary molars at an optimal position during and throughout self-fitting of the appliance over the maxillary teeth. The impression material 244 at the teeth receiving portions 252, 254 is transformed into a maxillary molar encasement during self-fitting of the interocclusal appliance of this eighth embodiment.

The fitting procedure in some respects is similar to that for other embodiments having a base or base plate and associated impression material described above. Just as with the embodiment of FIGS. 1-4, for a heat and fit procedure, the preform 240 is heated, such as by immersion in hot water, to soften the impression material 244 before the preform 240 is inserted over the teeth of the user's maxillary arch to transform into a maxillary molar encasement. The combination of the ledge 250 and the ridge 260 assist a user to install the preform 240 for a conforming fit. The user seats the tips of his incisor teeth on the base surface adjacent to the ridge 260 and between the ridge 260 of the base 242 and the ledge 260 of impression material 244. The ridge 260 guides the user to maintain at least a portion of the base top surface under the tips of the incisor teeth. The ledge 250 assists with shaping the softened impression material 244 so as to better conform to the space behind the user's front incisors and to contact the user's palate behind the user's front incisors. The spaces adjacent to the front ends 256, 258 of the ridges provide additional room for cuspid and/or bicuspid teeth, which have a greater tip diameter/depth than do incisors. As such, the spaces adjacent to the front ends 256, 258 permit the tips of cuspids/bicuspids to seat on the top surface of the base 242 during the fitting procedure.

A finished appliance according to this eighth embodiment (FIGS. 29-32 and 35) is not shown in the Figures. However, just as with the first embodiment shown in FIG. 4, for this eighth embodiment of the interocclusal appliance, no substantial impression material 244 contacts the front surface of the user's front teeth. No substantial impression material extends between the front teeth and the user's upper lip. However, the lower tips of the user's front teeth are supported by the top surface of the base material 242 and are appropriately positioned there with guidance from the ridge 260. Thus, a minor height of base material (e.g., the ridge 260) contacts the front surfaces of the user's front teeth. The molars are encased in impression material, but the front teeth are not so encased. Thus the interocclusal appliance is more comfortable to wear.

Referring next to FIG. 36, an alternate embodiment of the preform 240A of FIGS. 29 to 32 is shown. In this alternate embodiment, the base 242A has been modified to incorporate a series of bores 266 extending through the material forming the base. Such bores 266 provide air channels for greater breathing comfort when the interocclusal appliance is worn over the teeth. Bores 266 are shown as circular in FIG. 36, but may also be configured as slots or channels or any suitable alternative cross-sectional shape. Bores 266 are shown extending through the middle of the thickness of the base 242A, but also might be formed at the bottom surface of the base.

FIGS. 33 to 35 illustrate alternate cross sections for molar receiving portions of preforms to form interocclusal appliances according the present invention. Referring first to FIG. 35, which is a cross-sectional view of the preform 240 of FIG. 31, the impression material 244 is held in contact with the top surface of the base 242 between and over the side walls 241 formed in such base 242. In such an embodiment, a pilot channel is formed between the side walls 247, 248 to assist a user to seat the molars within the preform during fitting. Alternatively, referring to FIG. 33, a preform may be formed without pilot channels, such that the impression material 272 contacts the top surface of the base 270. As another alternative, the preform may have a base 280 with a concavely dished top surface and the impression material 282 may be held in contact with that dished surface. The outer edges of the dished top surface of the base 282 help to seat the molars within the interocclusal appliance formed from such preform.

To accommodate fitting persons with larger jaws whose rear teeth extend beyond the rear edges of the end portions of the base, excess impression material may be bonded at, near or in the receiving portions of the base of the two component preforms. Such excess impression material will flow beyond the end portions of the base, to encase or engage the user's rear teeth. In this way, a preform having a base with a shorter dental arch may be fitted to a user with a larger jaw. Hence, a smaller size preform may be offered that can still accommodate those users with larger jaw sizes. Unlike some current commercial products that have a larger base or tray that must be cut to shorten to fit users with smaller jaw sizes, the present invention can be formed with a commensurately smaller base. No cutting is needed. The impression material then can expand out of the base to fit users with larger jaws.

Many of the embodiments according to the invention described herein include a base in combination with an impression material, wherein the base is formed from a polymeric material that has a higher softening point temperature than does the impression material bonded or adhered thereto. Alternatively, it is within the scope of the invention herein to form a self-fitted interocclusal appliance with a single polymer material that has a softening point sufficient to be fitted to a user's maxillary or mandibular teeth and upon setting has a hardness sufficient to protect the user's teeth during bruxing or clenching events when the appliance is worn. For example, as shown in FIG. 12A, a preform 280 is formed with a single polymeric material (or mixture of materials) without a distinct separate base and impression material. While similar to the preform 80 of FIGS. 9-12, the preform 280 in FIG. 12A includes a lingual peripheral wall 282 but lacks buccal peripheral walls.

Suitable polymer materials that may be selected for a one-component preform include thermoset and thermoplastic polymers (or mixtures thereof wherein the polymers (or mixtures) have a Shore A hardness of at least 20. For example, alpha polyolefins mixed with ethylene vinyl acetate copolymers having 30% by weight or more of vinyl acetate for increased hardness may meet the rigorous requirements for a one component preform.

The invention has been illustrated by detailed description and examples of the preferred embodiments. Various changes in form and detail will be within the skill of persons skilled in the art. Therefore, the invention must be measured by the claims and not by the description of the examples or the preferred embodiments.

The invention claimed is:

1. An interocclusal appliance for fitting over maxillary teeth of a user, comprising:
a polymeric material formed in a configuration generally of a dental arch having a bottom plan surface and a top surface, and having first and second end portions and a central portion together forming said dental arch, wherein the first end portion defines a first receiving portion for receiving at least one maxillary molar, and the second end portion defines a second receiving portion for receiving at least one maxillary molar, and said central portion has a slanted ledge sloped downwardly from a maximum material thickness where the ledge contacts the first and second receiving portions to a minimum material thickness at an apex of the dental arch,
wherein upon heating the polymeric material to a temperature that is above its Vicat softening temperature, the receiving portions may be molded into cavities for receiving at least one maxillary molar, and said central portion may be shaped to conform to a portion of the user's palate behind one or more of the user's front teeth to form the interocclusal appliance; and
wherein said interocclusal appliance formed from said polymeric material lacks substantial material in front of the user's front teeth.

2. The interocclusal appliance of claim 1, wherein the end portions of the dental arch may be spaced further from one another by flexing the polymeric material.

3. The interocclusal appliance of claim 1, wherein the receiving portions releaseably fit over two or more of the user's maxillary molars, and once fitted, the appliance is maintained in fitted position in the user's mouth over such maxillary molars until the user elects to remove said appliance from the mouth.

4. The interocclusal appliance of claim 1, wherein a front tooth guide extends generally upwardly from a top surface of the dental arch at the central portion.

5. The interocclusal appliance of claim 4, wherein the front tooth guide comprises a continuous arcuate ridge.

6. The interocclusal appliance of claim 4, wherein the front tooth guide comprises one or more projections.

7. The interocclusal appliance of claim 1, wherein at least one inner upstanding ridge or lingual peripheral wall extends generally upwardly from the top surface of the dental arch.

8. The interocclusal appliance of claim 7, wherein the inner upstanding ridge extends from the first end portion to the second end portion along an entire lingual surface of the dental arch.

9. The interocclusal appliance of claim 7, wherein the at least one inner lingual upstanding ridge defines a maximum height and the central portion at its apex defines a minimum height of the appliance.

10. The interocclusal appliance of claim 1, wherein an outer upstanding ridge or buccal peripheral wall extends generally upwardly from a top surface of the dental arch at at least one end portion.

11. The interocclusal appliance of claim 1, wherein the polymeric material has a Shore A hardness of at least about 20.

12. The interocclusal appliance of claim 1, wherein the polymeric material comprises a material selected from the group consisting of: ethylene methyl acrylate (EMA) copolymers, ethylene vinyl acetate (EVA) copolymers, acrylics, high density polyethylenes (HDPE), styrenics (IMPS), acrylonitrile-butadiene-styrene (ABS) copolymers, poly(methylmethacrylates) (IM-PMMA), alpha-polyolefins, polypropylene, polycarbonate, polycaprolactam, polycaprolactone, polyurethanes, polyesters, and mixtures thereof.

13. The interocclusal appliance of claim 1, wherein the polymeric material comprises a resin or mixture of resins further incorporating a one or more types of larger particles or nanoparticles.

14. The interocclusal appliance of claim 13, wherein the particles are selected from the group consisting of pigments, colorants, plated clays, carbon fibrils, carbon nanotubes, and mixtures thereof.

15. The interocclusal appliance of claim 1, wherein the central portion defines at least one front teeth contacting surface.

16. An interocclusal appliance for fitting over maxillary or mandibular teeth of a user, comprising:
a preform comprising a base and an impression material, wherein the base has a bottom plan surface in a configuration of a dental arch having a first end portion, a second end portion and a central portion together forming said dental arch, and said base has a top surface and a bottom surface;
wherein the impression material is bonded to the top surface of said base, with said impression material defining a first receiving portion in the first end portion of the base for receiving one or more molars, and with said impression material defining a second receiving portion in the second end portion of the base for receiving one or more molars;
wherein said impression material further defines a slanted ledge at the central portion that is sloped downwardly from a maximum material thickness where the ledge contacts the first and second end portions to a minimum material thickness at an apex of the dental arch;
wherein said impression material comprises a polymeric material that has a Vicat softening temperature, and said base comprises a polymeric material, and upon heating the preform to a temperature that is above the Vicat softening temperature of the impression material polymeric material, the receiving portions may be molded into cavities for receiving at least one molar; and
wherein said interocclusal appliance formed from said preform contacts rear surfaces of at least some of the user's front teeth and lacks substantial polymeric material in front of the user's front teeth.

17. The interocclusal appliance of claim 16, further comprising at least one inner lingual upstanding ridge of impression material extending generally upwardly from the top surface of the dental arch.

18. The interocclusal appliance of claim 17, wherein the inner lingual upstanding ridge of impression material extends from the first end portion to the second end portion along an entire lingual surface of the preform.

19. The interocclusal appliance of claim 16, further comprising an outer buccal upstanding ridge extending generally upwardly from the top surface of the dental arch at at least one end portion.

20. The interocclusal appliance of claim 16, wherein the top surface of the base is either substantially flat, slanted, or concavely dished at at least one end portion.

21. The interocclusal appliance of claim 16, wherein a front tooth guide extends generally upwardly from a top surface of the dental arch at the central portion.

22. The interocclusal appliance of claim 21, wherein the front tooth guide comprises a continuous arcuate ridge.

23. The interocclusal appliance of claim 21, wherein the front tooth guide comprises one or more projections.

24. The interocclusal appliance of claim 16, wherein the appliance lacks polymeric material in contact with the tips of at least some of the user's front teeth.

25. The interocclusal appliance of claim 16, wherein the appliance has polymeric material in contact with at least some of the tips of the user's front teeth.

26. The interocclusal appliance of claim 16, wherein an air flow passage is formed within or under the central portion of the base.

27. The interocclusal appliance of claim 16, wherein at least one air flow passage is formed in the base.

28. The interocclusal appliance of claim 16, wherein the end portions of the base are spaced apart a first distance and may be separated to be spaced apart a second distance greater than the first distance by flexing the preform.

29. The interocclusal appliance of claim 28, wherein the second distance is greater than the first distance in the range of about 2 to about 35 mm.

30. The interocclusal appliance of claim 16, wherein the base defines at least one notch between one end portion and the central portion.

31. The interocclusal appliance of claim 16, wherein the receiving portions in the end portions of the base are shaped to receive one or more maxillary molars.

32. The interocclusal appliance of claim 16, wherein excess impression material is bonded at or near the receiving portions in the end portions of the base such that upon fitting the appliance said excess impression material may engage the user's rear teeth that extend beyond the end portions of the base.

33. The interocclusal appliance of claim 32, wherein the excess impression material engaging the rear teeth extends beyond the bottom plan surface of the base.

34. The interocclusal appliance of claim 16, wherein the polymeric material forming the base has a Shore A hardness of at least about 20.

35. The interocclusal appliance of claim 16, wherein the base comprises a polymeric material selected from the group consisting of: ethylene methyl acrylate (EMA) copolymers, acrylics, high density polyethylenes (HDPE), styrenics (IMPS), acrylonitrile-butadiene-styrene (ABS) copolymers, poly(methylmethacrylates) (IM-PMMA), polypropylene, polycarbonate, polycaprolactam, polycaprolactone, polyurethanes, polyesters, polypropylene-ethylene propylene diene monomer (PP/EPDM), thermoplastic vulcanizates (TPV), acrylic rubber TPV, styrene-butadiene-styrene (SBS) TPV, low density polyethylene (LDPE), polyvinylchoride (PVC), very low density polyethylene (VLDPE), styrene-butadiene copolymer (SBC) elastomer compounds, styrene-butadiene-styrene (SBS) linear block copolymers, styrene-isoprene-styrene (SIS) linear block copolymers, styrene-butadiene (SB)n branched copolymers, styrene-co-ethylene-butene-styrene (SEBS) linear block copolymers, styrene-co-ethylene-propylene (SEP) diblock copolymers, styrene-co-ethylene-ethylene-propylene-styrene (SEEPS) copolymers, mineral reinforced thermoplastic ethylene-styrene (TES/SEBS), polyethersulfone (PES), glass reinforced polyethersulfone, polyphenylsulfone (PPSU), styrene-acrylonitrile (SAN), acrylic-styrene-methylmethacrylate copolymers (NAS), polydimethylsilicone (PDMS), polyurea, silicone-polyurea, segmented polyurethane (SPU), perfluoroelastomer (FFKM), perfluoroelastomer (FEPM), chlorosulfonated polyethylene rubber, fluoroelastomer, silicone room temperature vulcanizate (RTV), cast polyurethane, chloroprene rubber, hydrogenated nitrile-butadiene rubber (HNBR), nitrile rubber, silicone rubber, perfuoroelastomer compounds (FFKT), and mixtures thereof.

36. The interocclusal appliance of claim 16, wherein the impression material comprises a polymeric material selected from the group consisting of: ethylene methyl acrylate (EMA) copolymers, ethylene vinyl acetate (EVA) copolymers, acrylics, high density polyethylenes (HDPE), styrenics (IMPS), acrylonitrile-butadiene-styrene (ABS) copolymers, poly(methylmethacrylates) (IM-PMMA),alpha-polyolefins, polypropylene-ethylene propylene diene monomer (PP/EPDM) thermoplastic vulcanizates (TPV), acrylic rubber TPV, styrene-butadiene-styrene (SBS) TPV, low density polyethylene (LDPE), polyvinylchoride (PVC), styrene-butadiene copolymer (SBC) elastomer compounds, styrene-butadiene-styrene (SBC) linear block copolymers, styrene-isoprene-styrene (SIS) linear block copolymers, styrene-butadiene (SB)n branched copolymers, styrene-co-ethylene-butene-styrene (SEBS) linear block copolymers, styrene-co-ethylene-propylene (SEP) diblock copolymers, styrene-co-ethylene-ethylene-propylene-styrene (SEEPS) copolymers, mineral reinforced thermoplastic ethylene-styrene (TES/SEBS), styrene-acrylonitrile (SAN), polydimethylsilicone (PDMS), polyurea, silicone-polyurea, segmented polyurethanes (SPU), perfluoroelastomer (FFKM), perfluoroelastomer (FEPM), chlorosulfonated polyethylene rubber, fluoroelastomer, silicone room temperature vulcanizate (RTV), cast polyurethane, chloroprene rubber, hydrogenated nitrile-butadiene rubber (HNBR), nitrile rubber, silicone rubber, perfuoroelastomer compounds (FFKT), and mixtures thereof.

37. The interocclusal appliance of claim 16, wherein impression material comprises from 0 to 85% by weight of an ethylene vinyl acetate copolymer having up to about 30% by weight vinyl acetate or mixture of such copolymers, and from 15 to 100% by weight of one or more alpha-polyolefins.

38. The interocclusal appliance of claim 37, wherein the ethylene vinyl acetate copolymer or mixture of such copolymers has less than about 10% by weight vinyl acetate.

39. The interocclusal appliance of claim 16, wherein the polymeric material forming the base has a Shore A hardness of at least 20 and the impression material comprises an ethylene vinyl acetate copolymer or mixture of said copolymers having from about 0 to about 30% by weight vinyl acetate.

40. The interocclusal appliance of claim 16, wherein the polymeric material of the base further incorporates one or more types of larger particles or nanoparticles.

41. The interocclusal appliance of claim 40, wherein the nanoparticles are selected from the group consisting of pigments, colorants, plated clays, carbon fibrils, carbon nanotubes, and mixtures thereof.

42. The interocclusal appliance of claim 16, wherein the polymeric material of the impression material further incorporates one or more types of larger particles or nanoparticles.

43. The interocclusal appliance of claim 42, wherein the nanoparticles are selected from the group consisting of pigments, colorants, plated clays, carbon fibrils, carbon nanotubes, and mixtures thereof.

44. The interocclusal appliance of claim 16, wherein said central portion is shaped so as to be disposed behind and in contact with at least some of the user's front teeth.

45. The interocclusal appliance of claim 16, wherein the first buccal peripheral wall slopes downwardly from a rear portion of the preform to a labial face of the preform at the central portion.

46. The interocclusal appliance of claim 16, wherein the impression material is present in an amount from about 3.5 g to about 7.0 g of material.

47. The interocclusal appliance of claim 16, wherein upon heating the impression material polymeric material to a temperature that is above its Vicat softening temperature, said central portion may be shaped to conform to a portion of the user's palate behind one or more of the user's front teeth to form the interocclusal appliance.

* * * * *